(12) United States Patent
Reynolds et al.

(10) Patent No.: US 11,229,603 B1
(45) Date of Patent: Jan. 25, 2022

(54) ENHANCED RODEFERIN BROAD SPECTRUM

(71) Applicant: Reynolds Blue LLC, Scottsdale, AZ (US)

(72) Inventors: Rodney Reynolds, Scottsdale, AZ (US); Carmine Russo, Tucson, AZ (US); Robert Reynolds, Scottsdale, AZ (US)

(73) Assignee: Reynolds Blue, LLC, Scottsdale, AZ (US)

( * ) Notice: Subject to any disclaimer, the term of this patent is extended or adjusted under 35 U.S.C. 154(b) by 0 days.

(21) Appl. No.: 17/391,023

(22) Filed: Aug. 1, 2021

Related U.S. Application Data

(60) Provisional application No. 63/142,492, filed on Jan. 27, 2021, provisional application No. 63/060,119, filed on Sep. 24, 2020.

(51) Int. Cl.
| | | |
|---|---|---|
| *A61K 9/127* | (2006.01) | |
| *A61K 47/24* | (2006.01) | |
| *A61K 33/00* | (2006.01) | |
| *A61K 33/38* | (2006.01) | |
| *A61K 33/242* | (2019.01) | |
| *A61K 33/30* | (2006.01) | |
| *A61K 33/36* | (2006.01) | |
| *A61K 33/34* | (2006.01) | |
| *A61K 33/18* | (2006.01) | |
| *A61K 33/243* | (2019.01) | |
| *A61K 33/24* | (2019.01) | |
| *A61K 33/32* | (2006.01) | |
| *A61K 33/26* | (2006.01) | |
| *A61K 47/10* | (2017.01) | |
| *A61K 47/28* | (2006.01) | |
| *A61K 31/5415* | (2006.01) | |

(52) U.S. Cl.
CPC ........ *A61K 9/1277* (2013.01); *A61K 31/5415* (2013.01); *A61K 33/00* (2013.01); *A61K 33/18* (2013.01); *A61K 33/24* (2013.01); *A61K 33/242* (2019.01); *A61K 33/243* (2019.01); *A61K 33/26* (2013.01); *A61K 33/30* (2013.01); *A61K 33/32* (2013.01); *A61K 33/34* (2013.01); *A61K 33/36* (2013.01); *A61K 33/38* (2013.01); *A61K 47/10* (2013.01); *A61K 47/24* (2013.01); *A61K 47/28* (2013.01)

(58) Field of Classification Search
CPC .... A61K 31/5415; A01N 55/02; A01N 59/16; A01N 59/20; A01N 43/84; A01N 25/28
See application file for complete search history.

(56) References Cited

U.S. PATENT DOCUMENTS

2008/0031960 A1* 2/2008 Wilson .................. A01N 59/16 424/489

OTHER PUBLICATIONS

Boccalini et al. "Methylene blue-containing liposomes as new photodynamic anti-bacterial agents" Journal of Materials Chemistry B. 5, 2788-2797 (Year: 2017).*

* cited by examiner

*Primary Examiner* — Kortney L. Klinkel
(74) *Attorney, Agent, or Firm* — Eugene Vamos

(57) ABSTRACT

This process manufactures a finished medicine that can be used against broad spectrum, Anti-Viral, Anti-Bacterial, Anti-Fungal, and Anti-parasitic disease conditions that attack the human body but not limited to other medical conditions and or other types of treatments use for animals other than humans.

20 Claims, 4 Drawing Sheets

US 11,229,603 B1

ENHANCED RODEFERIN BROAD SPECTRUM

CROSS-REFERENCE TO RELATED APPLICATIONS

This application claims the priority benefit to U.S. Provisional Application 63/142,492 dated Jan. 27, 2021 and the priority benefit to U.S. Provisional Application 63/060,119 dated Sep. 24, 2020

STATEMENT REGARDING FEDERALLY SPONSORED RESEARCH & DEVELOPMENT

Not Applicable

THE NAMES OF THE PARTIES TO A JOINT RESEARCH AGREEMENT

Not Applicable

REFERENCE TO A "SEQUENCE LISTING," A TABLE, OR A COMPUTER PROGRAM

Not Applicable

STATEMENT REGARDING PRIOR DISCLOSURES BY AN INVENTOR OR JOINT INVENTOR

Not Applicable

BACKGROUND OF THE INVENTION

Field of Invention

The present invention generally relates to the field of substances for medical purposes.

This product can be used as a broad spectrum, Anti-Viral, Anti-Bacterial, Anti-Fungal, and Anti-parasitic disease conditions, that attack the human body but not limited to other medical conditions and or other types of treatments use for animals other than human.

DESCRIPTION OF THE INVENTION

Figure 1:
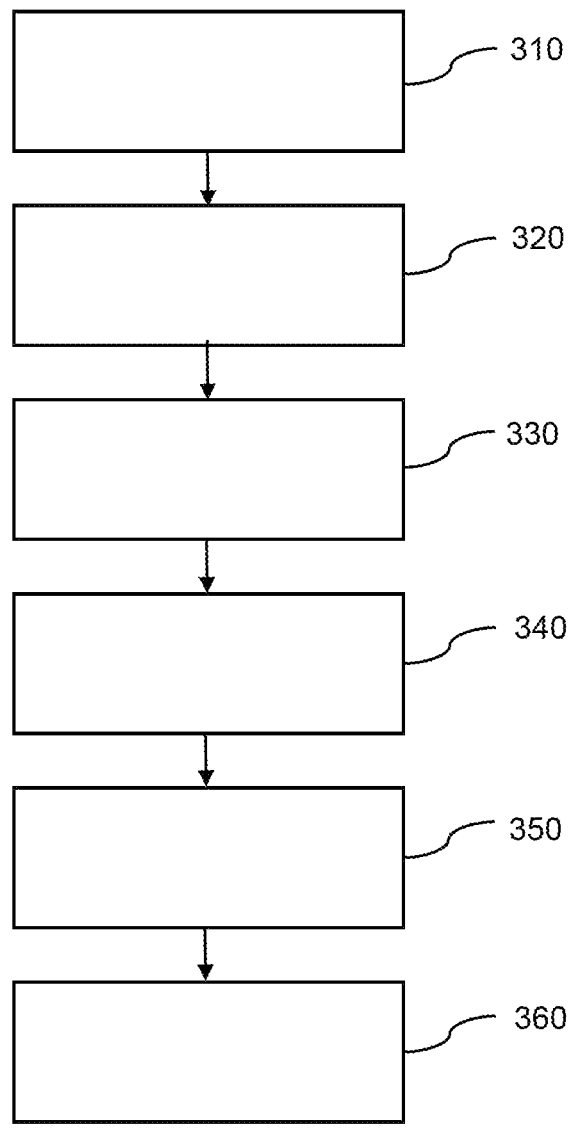
FIG. 1 is a flow chart of the process steps for the generalized manufacture of Rodeferin.

Rodeferin is a medicine that simply enhances the known medical actions of Methylene Blue also known as methylthioninium chloride in the human body.

Rodeferin can be taken Intravenously, Nebulized, or sublingualy, and not limited to orally ingesting it or as a topical application to the skin.

Rodeferin contains numerous types of colloidal metallic and or non-metallic nano particles used singularly or in combination and may be in both ionic or non-ionic forms also used singularly and or in combination.

The most effective colloid type is usually a sol but this is no limited to other colloidal forms such as an emulsion, foam, and or aerosol.

Once the proper colloidal mixture is selected, it is then wrapped and incased into a lyposome of at least one lipid bilayer but not limited to multi layer lyposome's.

Finally, the Methylene Blue suspension is then coated onto the outermost layer of the lyposome's containing the colloidal mixture.

The known medical actions of Methylene Blue is now greatly enhanced by the movement of electrons to and from the colloidial mixture that is wrapped inside the liposome. The dosing levels of the Methylene Blue can now be greatly reduced while its efficacy greatly enhanced.

Ingredients of Rodeferin

1. Main Active Ingredient—Methylene Blue or methylthioninium chloride, medical grade powder dissolved in IV type sterile water in a recommended solution range from 0.25% to 2% but not limited to other solution percentages. It is recommended to filter this methylthioninium chloride solution down to at least 100 nm for IV use and at least zoo nm for all other uses. The percentage by volume of the methylthioninium chloride solution in the finished medicine can be as low as 5% and as high at 95%. It is recommended to use a 1% methylthioninium chloride solution at 25% by volume in the finished medicine.

2. Lipid Bilayer material—Any FDA approved phospholipid, single and or multi layer material to wrap the colloids in and attach the Methylene Blue to can be used. The Lipid Bilayer material is dissolved in a solution, at a ratio per the manufacturer's recommended specifications. The percentage by volume of the Lipid Bilayer material solution can be as low as 5% and as high as 95% in the finished medicine. It is recommended to use this Lipid Bilayer material solution at 25% by volume in the finished medicine. It is recommended to use phosphatidylcholine as the Lipid Bilayer Material; use at least 90% pure for oral application and at least 95% or purer for IV application. If phosphatidylcholine is used as a Lipid Bilayer material in the Lipid Bilayer material solution, it is recommended to use it as a 10% solution with Sodium Deoxycholate 4.2% and Benzyl Alcohol 0.9% mixed in sterile water.

3. Supporting Colloid Mechanism—At least five known methods can be used to manufacture colloids including but not limited to Grind, Wave, Liquid, Chemical, Electrical. For medical or health purposes, the FDA allows both the grind and electrical manufacturing techniques to be used. We recommend electrical manufacturing techniques that produce colloid particles with sizes between 10 to 100 nano-meters that are suspended in de-ionized water at a rate of 20 ppm to 300 ppm. Larger or smaller particle sizes can work and higher or lower PPM values can also be used however the recommended values appear to work best. Colloids that have been tested and can be used to support the Methylene Blue's actions include but are not limited to Silver, Gold, Silica, Copper, Zinc, Iodine, Titanium, Platinum, Palladium, Iridium, rhodium, osmium, iron, and manganese. We recommend using two metals and one non metal however different combinations can also work. If an IV version of the medicine is to be manufactured then it is recommended to use particle sizes no greater than 100 nm. Depending on the PPM values of the colloids and the particle sizes, the percentage by volume of the colloid solution in the finished medicine can be as low as 5% and as high at 95%. It is recommended to use this material at 50% by volume if the particle sizes range from 10 to 100 nano-meters and the PPM values range between 20 ppm and 300 ppm.

Generalized Manufacture of Rodeferin

The generalized method for making Rodefering comprises the steps of:
(a) placing colloids (120) in a vial and immersing the vial in a solution within an ultrasonic device (310);
(b) mixing the colloids (120) within the vial with the ultrasonic device (320);
(c) adding a lipid bilayer material solution (130) to the colloids (120) in the vial (330);
(d) mixing the lipid bilayer material solution (130) and the colloids (120) in the vial with the ultrasonic device (340);
(e) adding a methylthioninium chloride solution (140) to the lipid bilayer material solution (130) and the colloids (120) in the vial (350);
(f) mixing the methylthioninium chloride solution (140), the lipid bilayer material solution (130), and the colloids (120) in the vial with the ultrasonic device resulting in a finished medicine (150) (360).

FIG. 1 shows a flow chart of the process steps for the generalized manufacture of Rodeferin.

Figure 2:
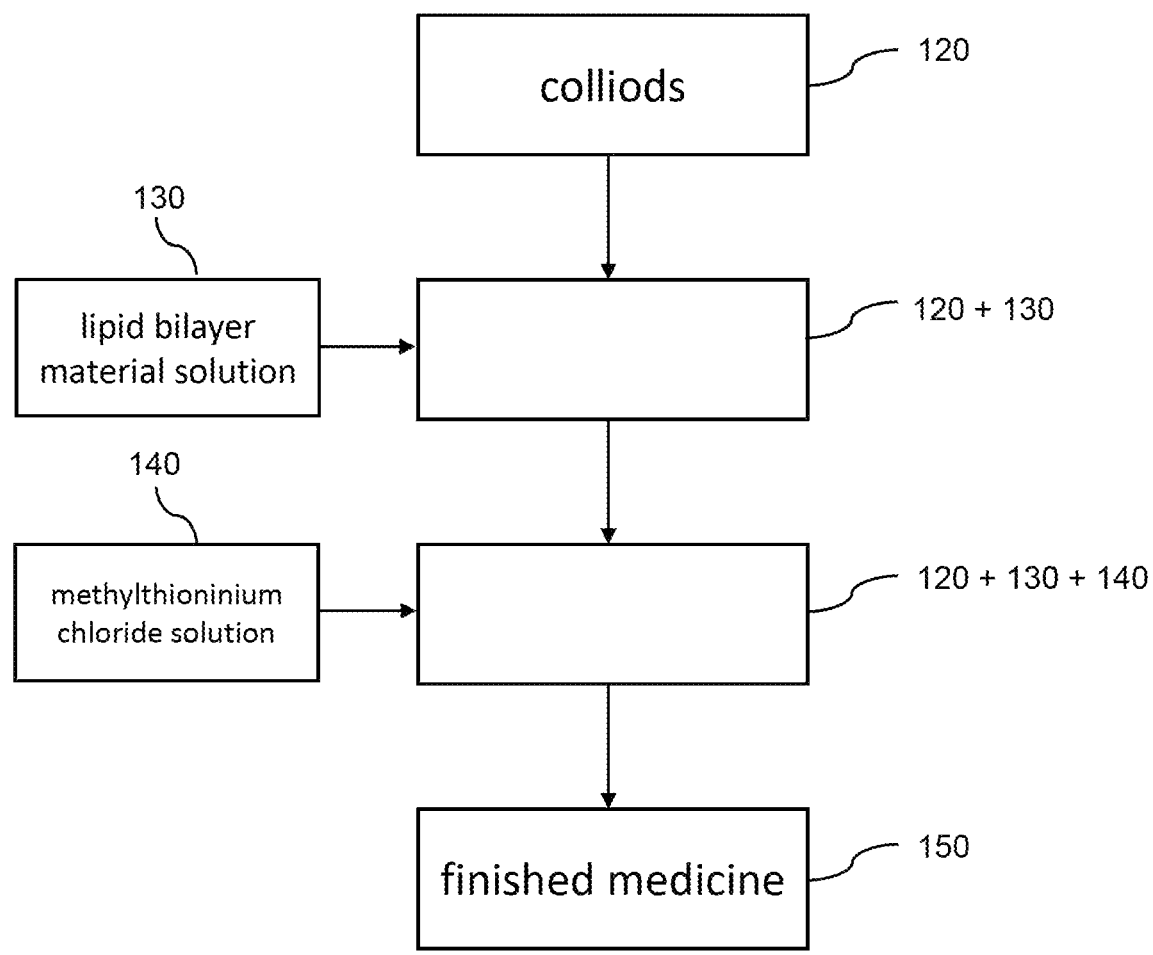
FIG. 2 is a materials mixing flow chart for the manufacture of Rodeferin within the process steps for the generalized manufacture of Rodeferin.

FIG. 2 is a materials mixing flow chart for the manufacture of Rodeferin within the process steps for the generalized manufacture of Rodeferin First Example of How to Manufacture 60 ml of Rodeferin IV Version using Gold, Silver, and Silica Recommended Ratios of ingredients 25% MB-25% Lipid-50% Colloids 15 ml of Methylene Blue—made at a 1% solution in sterile water filtered to 100 nm 8 ml of Colloidal Gold Solution less than 100 nm and at 20 ppm-20% Ionic particles 12 ml of Colloidal Silver Solution less than 100 nm and at 20 ppm-20% Ionic particles 10 ml of Colloidal Silica Solution less than 100 nm and at 60 ppm-20% Ionic particles 15 ml of Phosphatidylcholine Solution Phosphatidylcholine/ml, as 100 mg with Sodium Deoxycholate 42 mg with Sodium Hydroxide 0.37 mg and Benzyl Alcohol 0.9% in sterile water.

Recommended Mixing Process

Combine the three colloids in a sealed vial that will hold at least 60 ml of medicine. Suspend the vial in an ultrasound device to mix. We recommend immersing the vial in a solution of 20% isopropyl alcohol and water or one part alcohol to five parts water and to mix it at a frequency rate of 42-KHZ for 15 minutes.

Note: Suspending the vial in other solutions and or different ratios of alcohol to water and mixing for longer or shorter periods and at varying frequency ranges will also work. If other than glass vials are used such as plastic, metal, composite, small, medium and large industrial vessels, tanks; times or different frequencies might be required to allow the sound waves to pass through the container and mix the particles correctly.

Once the colloids are mixed add the 15 ml of Phosphatidylcholine Solution to the vial and mix for another 15 minutes to wrap the colloids in the lipid (340). Finally add the 15 ml of Methylene Blue (350) and mix for another 15 minutes to coat the outside of the lipid containing the colloids, resulting in a finished medicine (150) (360).

Second Example of how to Manufacture Rodeferin Using Gold, Silver, and Silica

Raw Ingredients:
Methylene Blue 1% medical grade IV able solution in sterile water (200)
Colloidal Gold Solution (210) (0.9999 Pure Gold in Colloidal form)
Colloidal Silver Solution (220) (0.9999 Pure Silver in Colloidal form)
Colloidal Silica Solution (230) (0.999 Pure Silica in Colloidal form)
Phosphatidylcholine/ml, as 100 mg with Sodium Deoxycholate 42 mg with Sodium Hydroxide 0.37 mg and Benzyl Alcohol 0.9% in sterile water, not limited to other forms (240)

Ratios of Ingredients:
15 ml Methylene Blue Solution (200)
From 1 cc-16 cc Colloidal Gold Solution (210)
From 1 cc-25 cc Colloidal Silver Solution (220)
From 1 cc-20 cc Colloidal Silica Solution (230)
From 2 cc-30 cc Phosphatidylcholine Solution (240)

Mixing Process:
(Part A)
Take 15 ml of Methylene Blue Solution (200) and Filter once with a 0.22 micron filter. Then filter remaining mixture with a 0.1 micron filter (400).

(Part B)
Separately filter Colloidal Gold Solution (210) with a 0.1 micron filter (410).
Separately filter Colloidal Silver Solution (220) with a 0.1 micron filter (420).
Separately filter Colloidal Silica Solution (230) with a 0.1 micron filter (430).
Add Phosphatidylcholine Solution (240)
Combine filtered colloidal solutions from Part B (210, 220, 230) forming a first combined solution (250) in a sealed vial (440). Suspend the first combined solution (250) in an ultrasound device using 20% isopropyl alcohol and water or alternatively 1 part alcohol to 5 parts water for 15 minutes (450). Take this first combined solution (250) out of the ultrasound (460) and add Phosphatidylcholine Solution (240) forming a second combined solution (260) (470). Take this second combined solution (260) and suspend the second combined solution (260) in an ultrasound device using 20% isopropyl alcohol or alternatively 1 part alcohol to 5 parts water for 15 minutes (480).

(Part C)
Add 15 ml of the filtered Methylene Blue Solution (200) with the second combined solution (260) forming a third combined solution (270) (490). Suspend the third combined solution (270) with an ultrasound device using 20% isopropyl alcohol and water or alternatively 1 part alcohol to 5 parts water for 15 minutes (500), resulting in a finished medicine (280).

Figure 3:
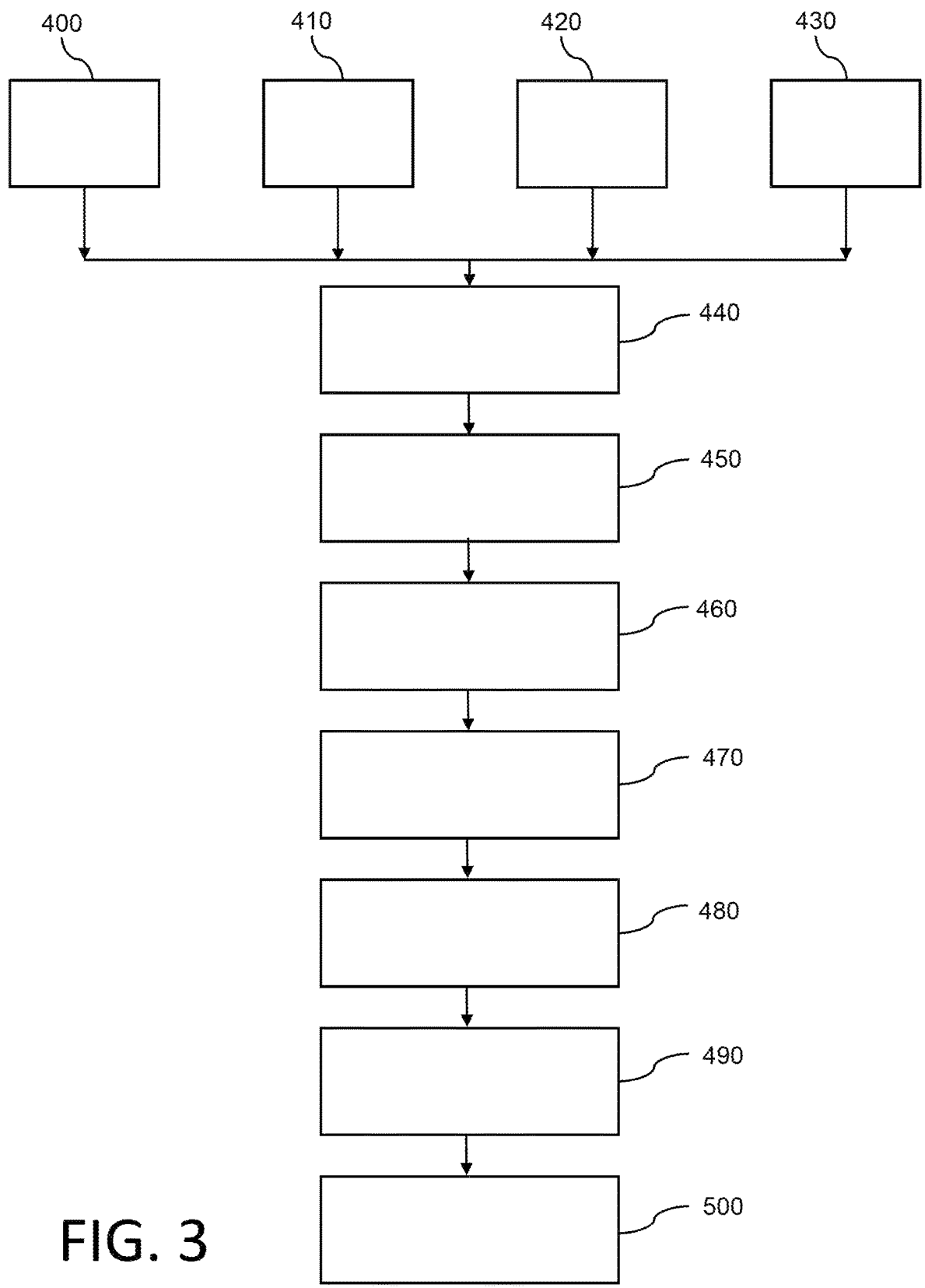
FIG. 3 is a flow chart of the process steps for the second example for the manufacture of Rodeferin using Gold, Silver and Silica.

FIG. 3 shows a flow chart of the process steps for the second example for the manufacture of Rodeferin using Gold, Silver and Silica.

Figure 4:
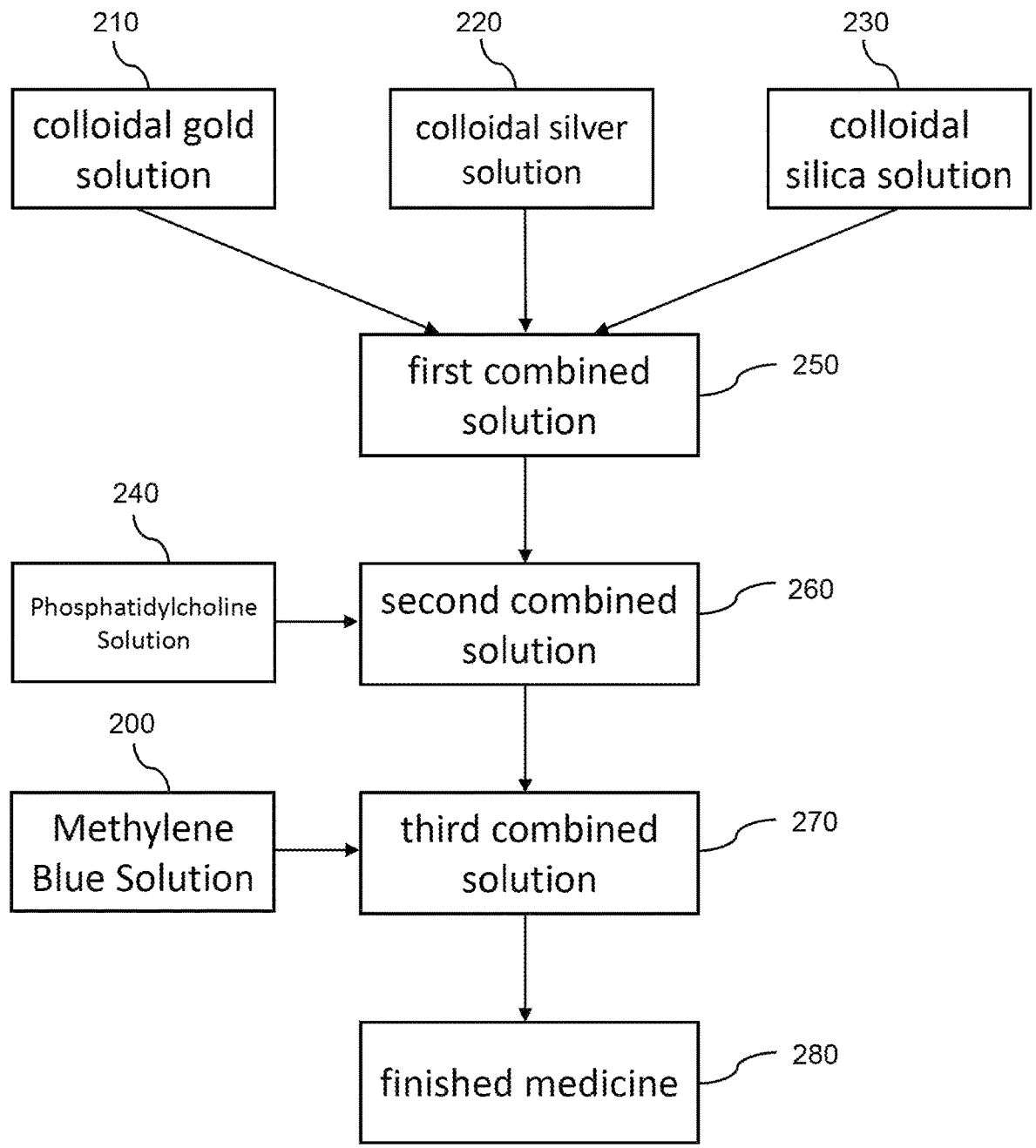
FIG. 4 is a materials mixing flow chart for the manufacture of Rodeferin within the process steps for the second example for the manufacture of Rodeferin using Gold, Silver and Silica.

FIG. 4 is a materials mixing flow chart for the manufacture of Rodeferin within the process steps for the second example for the manufacture of Rodeferin using Gold, Silver and Silica.

Using Rodeferin
1. IV Therapy: It is recommended to add 1 ml of Rodeferin per 100 cc of Dextrose 5% delivered via IV 2. Nebulizing: The IV version the recommended medicine type for aerosolizing. Add ½ ml of Rodeferin 3-4 cc of nebulizing solution. Breathe for TO minutes with masked nebulizer.

3. Oral therapy: The IV version is more pure and can be used sublingually even though manufacturing an oral version does not require the purest form of a lipid and or require 100 NM and smaller sized particles. Hold ½ ml under the tongue for approximately 10 minutes & then swallow remaining medicine.

4. Other uses: Delivery system into the body may not be limited to items 1 thru 3 and may include other delivery methods.

Additional Comments

While the foregoing written description of the invention enables a person having ordinary skill in the art to make and use what is considered presently to be the best mode thereof, those of ordinary skill in the art will understand and appreciate the existence of variations, combinations, and equivalents of the specific embodiment, process, and examples herein. The invention should therefore not be limited by the above described embodiment, process, and examples, but by all embodiments and processes within the scope and spirit of the invention.

BRIEF DESCRIPTION OF THE SEVERAL VIEWS OF THE DRAWING

Not Applicable

SEQUENCE LISTING

Not Applicable

We claim:

1. A method for manufacturing a finished medicine, the method comprising of the steps of:
   (a) placing colloids in a vial and immersing the vial in a solution within an ultrasonic device;
   (b) mixing the colloids within the vial with the ultrasonic device;
   (c) adding a lipid bilayer material solution to the colloids in the vial;
   (d) mixing the lipid bilayer material solution and the colloids in the vial with the ultrasonic device;
   (e) adding a methylthioninium chloride solution to the lipid bilayer material solution and the colloids in the vial;
   (f) mixing the methylthioninium chloride solution, the lipid bilayer material solution, and the colloids in the vial with the ultrasonic device resulting in the finished medicine;
   (g) where the colloids ranges from 5% to 95% by volume in the finished medicine,
   (h) where the lipid bilayer material solution ranges from 5% to 95% by volume in the finished medicine,
   (i) where the methylthioninium chloride solution ranges from 5% to 95% by volume in the finished medicine.

2. The method for manufacturing a finished medicine as described in claim 1,
   (a) where the concentration of colloid particles in the colloids ranges between 20 ppm and 300 ppm.

3. The method for manufacturing a finished medicine as described in claim 2,
   (a) where the colloid particles are selected from one or more of the group consisting of Silver, Gold, Silica, Copper, Zinc, Iodine, Titanium, Platinum, Palladium, Iridium, Rhodium, Osmium, Iron, and Manganese,
   (b) where the colloid particles range between 10 to 100 nm in size.

4. The method for manufacturing a finished medicine as described in claim 2,
   (a) where the colloid particles are selected from two metals and one non-metal,
   (b) where the colloid particles range between 10 to 100 nm in size.

5. The method for manufacturing a finished medicine as described in claim 1,
   (a) where the lipid bilayer material is dissolved in the lipid bilayer material solution at a ratio sufficient to form a liposome around the colloids,
   (b) where the lipid bilayer material solution further comprises 4.2% by volume Sodium Deoxycholate and 0.9% by volume Benzyl Alcohol.

6. The method for manufacturing a finished medicine as described in claim 3,
   (a) where the lipid bilayer material is phosphatidylcholine.

7. The method for manufacturing a finished medicine as described in claim 6,
   (a) where the lipid bilayer material solution is 25% by volume in the finished medicine.

8. The method for manufacturing a finished medicine as described in claim 6,
   (a) where the lipid bilayer material is a 10% solution in the lipid bilayer material solution,
   (b) where the lipid bilayer material solution further comprises 4.2% by volume Sodium Deoxycholate and 0.9% by volume Benzyl Alcohol.

9. The method for manufacturing a finished medicine as described in claim 6,
   (a) where the lipid bilayer material is dissolved in the lipid bilayer material solution at a ratio sufficient to form a liposome around the colloids,
   (b) where the lipid bilayer material solution further comprises 4.2% by volume Sodium Deoxycholate and 0.9% by volume Benzyl Alcohol.

10. The method for manufacturing a finished medicine as described in claim 6,
    (a) where the methylthioninium chloride in the methylthioninium chloride solution ranges from 0.25% to 2% by volume.

11. The method for manufacturing a finished medicine as described in claim 8,
    (a) where the methylthioninium chloride in the methylthioninium chloride solution ranges from 0.25% to 2% by volume.

12. A method for manufacturing a finished medicine, the method comprising of the steps of:
    (a) filtering a 15 ml 1% methylene blue solution with a 0.22 micron filter and then with a 0.1 micron filter;
    (b) filtering a 1 cc-16 cc colloidal gold solution with a 0.1 micron filter;
    (c) filtering a 1 cc-16 cc colloidal silver solution with a 0.1 micron filter;
    (d) filtering a 1 cc-16 cc colloidal silica solution with a 0.1 micron filter;
    (e) combining the filtered colloidal gold solution, the filtered colloidal silver solution, and the filtered colloidal silica solution forming a first combined solution in a sealed vial;
    (f) suspending the first combined solution in an ultrasound device using 20% isopropyl alcohol and water for 15 minutes;

(g) taking the first combined solution out of the ultrasound device;
(h) adding a 2 cc-30 cc phosphatidylcholine solution to the first combined solution forming a second combined solution;
(i) suspending the second combined solution in the ultrasound device using 20% isopropyl alcohol and water for 15 minutes;
(j) combining the 15 ml filtered methylene blue solution with the second combined solution forming a third combined solution;
(k) suspending the third combined solution in the ultrasound device using 20% isopropyl alcohol and water for 15 minutes, resulting in the finished medicine.

13. The method for manufacturing a finished medicine as described in claim 12,
(a) where the concentration of the colloidal gold in the colloidal gold solution ranges between 20 ppm and 300 ppm;
(b) where the concentration of the colloidal silver in the colloidal silver solution ranges between 20 ppm and 300 ppm;
(c) where the concentration of the colloidal silica in the colloidal silica solution ranges between 20 ppm and 300 ppm.

14. A method for manufacturing a finished medicine, the method comprising of the steps of:
(a) placing colloids in a container and immersing the container in a solution within an ultrasonic device;
(b) mixing the colloids within the container with the ultrasonic device;
(c) adding a lipid bilayer material solution to the colloids in the container;
(d) mixing the lipid bilayer material solution and the colloids in the container with the ultrasonic device;
(e) adding a methylthioninium chloride solution to the lipid bilayer material solution and the colloids in the container;
(f) mixing the methylthioninium chloride solution, the lipid bilayer material solution, and the colloids in the container with the ultrasonic device resulting in the finished medicine;
(g) where the colloids ranges from 5% to 95% by volume in the finished medicine,
(h) where the lipid bilayer material solution ranges from 5% to 95% by volume in the finished medicine,
(i) where the methylthioninium chloride solution ranges from 5% to 95% by volume in the finished medicine,
(j) where the container allows the passing through of sound waves.

15. The method for manufacturing a finished medicine as described in claim 14,
(a) where the concentration of colloid particles in the colloids ranges between 20 ppm and 300 ppm.

16. The method for manufacturing a finished medicine as described in claim 15,
(a) where the colloid particles are selected from one or more of the group consisting of Silver, Gold, Silica, Copper, Zinc, Iodine, Titanium, Platinum, Palladium, Iridium, Rhodium, Osmium, Iron, and Manganese,
(b) where the colloid particles range between 10 to 100 nm in size.

17. The method for manufacturing a finished medicine as described in claim 15,
(a) where the colloid particles are selected from two metals and one non-metal,
(b) where the colloid particles range between 10 to 100 nm in size.

18. The method for manufacturing a finished medicine as described in claim 14,
(a) where the lipid bilayer material is dissolved in the lipid bilayer material solution at a ratio sufficient to form a liposome around the colloids,
(b) where the lipid bilayer material solution further comprises 4.2% by volume Sodium Deoxycholate and 0.9% by volume Benzyl Alcohol.

19. The method for manufacturing a finished medicine as described in claim 16,
(a) where the lipid bilayer material is phosphatidylcholine.

20. The method for manufacturing a finished medicine as described in claim 19,
(a) where the lipid bilayer material solution is 25% by volume in the finished medicine.

\* \* \* \* \*